US00PP32165P2

(12) United States Plant Patent
Kolster et al.

(10) Patent No.: US PP32,165 P2
(45) Date of Patent: Sep. 8, 2020

(54) ***HYDRANGEA* PLANT NAMED 'HOKOMAGREVO'**

(50) Latin Name: *Hydrangea macrophylla*
Varietal Denomination: Hokomagrevo

(71) Applicants: KOLSTER HOLDING B.V., Boskoop (NL); HORTEVE BREEDING B.V., Aalsmeer (NL)

(72) Inventors: Peter R. Kolster, Boskoop (NL); Cornelis P. Eveleens, Aalsmeer (NL)

(73) Assignees: Kolster Holding B.V., Boskoop (NL); Horteve Breeding B.V., Aalsmeer (NL)

( * ) Notice: Subject to any disclaimer, the term of this patent is extended or adjusted under 35 U.S.C. 154(b) by 0 days.

(21) Appl. No.: 16/602,296

(22) Filed: Sep. 6, 2019

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Hydrangea* plant named 'Hokomagrevo', characterized by its compact, upright and somewhat outwardly spreading plant habit; moderately vigorous to vigorous growth habit and moderate growth rate; freely branching habit with strong and thick sturdy stems; freely flowering habit; compact mophead-type inflorescences with green, white and light purple-colored sterile flowers; and good postproduction longevity.

2 Drawing Sheets

Figure 1:
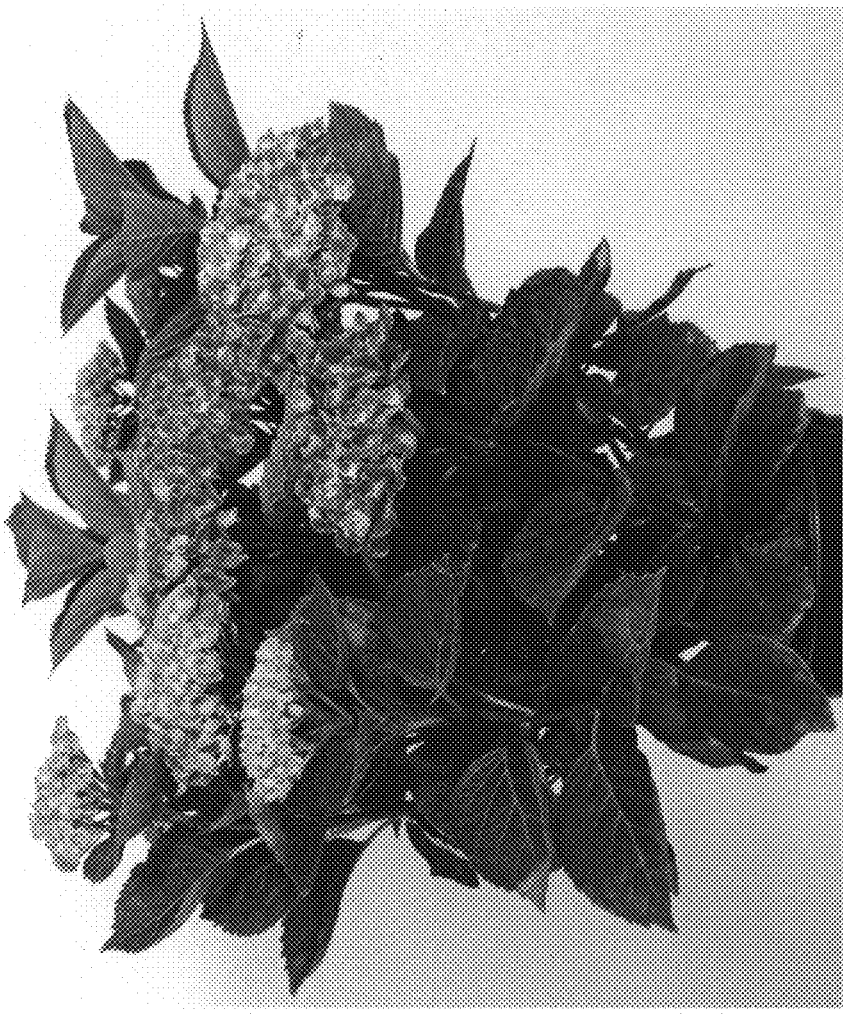

Botanical designation: *Hydrangea macrophylla.*
Cultivar denomination: 'HOKOMAGREVO'.

CROSS-REFERENCED TO CLOSELY-RELATED APPLICATIONS

Title: *Hydrangea* Plant Named 'HOKOMARORE'
Applicants: Cornelis P. Eveleens & Peter R. Kolster
Ser. No. 15/999,929

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'Hokomagrevo'.

The new *Hydrangea* is a naturally-occurring whole plant mutation of *Hydrangea macrophylla* 'Hokomarevo', disclosed in U.S. Plant Pat. No. 22,260. The new *Hydrangea* plant was discovered and selected by the Inventors as a single flowering plant from within a population of plants of 'Hokomarevo' in a controlled greenhouse environment in Boskoop, The Netherlands on Jun. 24, 2015.

Asexual reproduction of the new *Hydrangea* plant by vegetative terminal cuttings in a controlled environment in Boskoop, The Netherlands since August, 2015 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Hokomagrevo'. These characteristics in combination distinguish 'Hokomagrevo' as a new and distinct *Hydrangea* plant:

1. Compact, upright and somewhat outwardly spreading plant habit.
2. Moderately vigorous to vigorous growth habit and moderate growth rate.
3. Freely branching habit with strong and thick sturdy stems.
4. Freely flowering habit.
5. Compact mophead-type inflorescences with green, white and light purple-colored sterile flowers.
6. Good postproduction longevity.

Plants of the new *Hydrangea* can be compared to plants of the mutation parent, 'Hokomarevo'. Plants of the new *Hydrangea* differ primarily from plants of 'Hokomarevo' in sterile flower color as sterile flower sepals of plants of the new *Hydrangea* are green, white and light purple in color whereas sterile flower sepals of plants of 'Hokomarevo' are red purple in color becoming red purple and green with development.

Plants of the new *Hydrangea* can be compared to plants of *Hydrangea macrophylla* 'Hokomarore', disclosed in U.S. Plant patent application Ser. No. 15/999,929. Plants of the new *Hydrangea* differ primarily from plants of 'Hokomarore' in sterile flower color as sterile flower sepals of plants of the new *Hydrangea* are green, white and light purple in color whereas sterile flower sepals of plants of 'Hokomarore' are red purple in color.

Plants of the new *Hydrangea* can be compared to plants of the *Hydrangea macrophylla* 'Hokomathyst', disclosed in U.S. Plant Pat. No. 22,261. In side-by-side comparisons plants of the new *Hydrangea* differ primarily from plants of 'Hokomathyst' in the following characteristics:

1. Plants of the new *Hydrangea* are more compact than plants of 'Hokomathyst'.
2. Plants of the new *Hydrangea* are more outwardly spreading than and not as upright as plants of 'Hokomathyst'.
3. Plants of the new *Hydrangea* have smaller inflorescences than plants of 'Hokomathyst'.
4. Plants of the new *Hydrangea* differ from plants of 'Hokomathyst' in sterile flower color as sterile flower sepals of plants of the new *Hydrangea* are green, white and light purple in color whereas sterile flower sepals of plants of 'Hokomathyst' are red purple in color with green-colored margins.

Plants of the new *Hydrangea* can be compared to plants of the *Hydrangea macrophylla* 'Hortmagreclo', disclosed in U.S. Plant Pat. No. 28,063. In side-by-side comparisons plants of the new *Hydrangea* differ primarily from plants of 'Hortmagreclo' in the following characteristics:

1. Plants of the new *Hydrangea* are more compact than plants of 'Hortmagreclo'.
2. Plants of the new *Hydrangea* have smaller inflorescences than plants of 'Hortmagreclo'.
3. Plants of the new *Hydrangea* differ from plants of 'Hortmagreclo' in sterile flower color as sterile flower sepals of plants of the new *Hydrangea* are green, white and light purple in color whereas sterile flower sepals of plants of 'Hortmagreclo' are green to dark green in color.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1 of 2) is a side perspective view of a typical flowering plant of 'Hokomagrevo' grown in a container.

Figure 2:
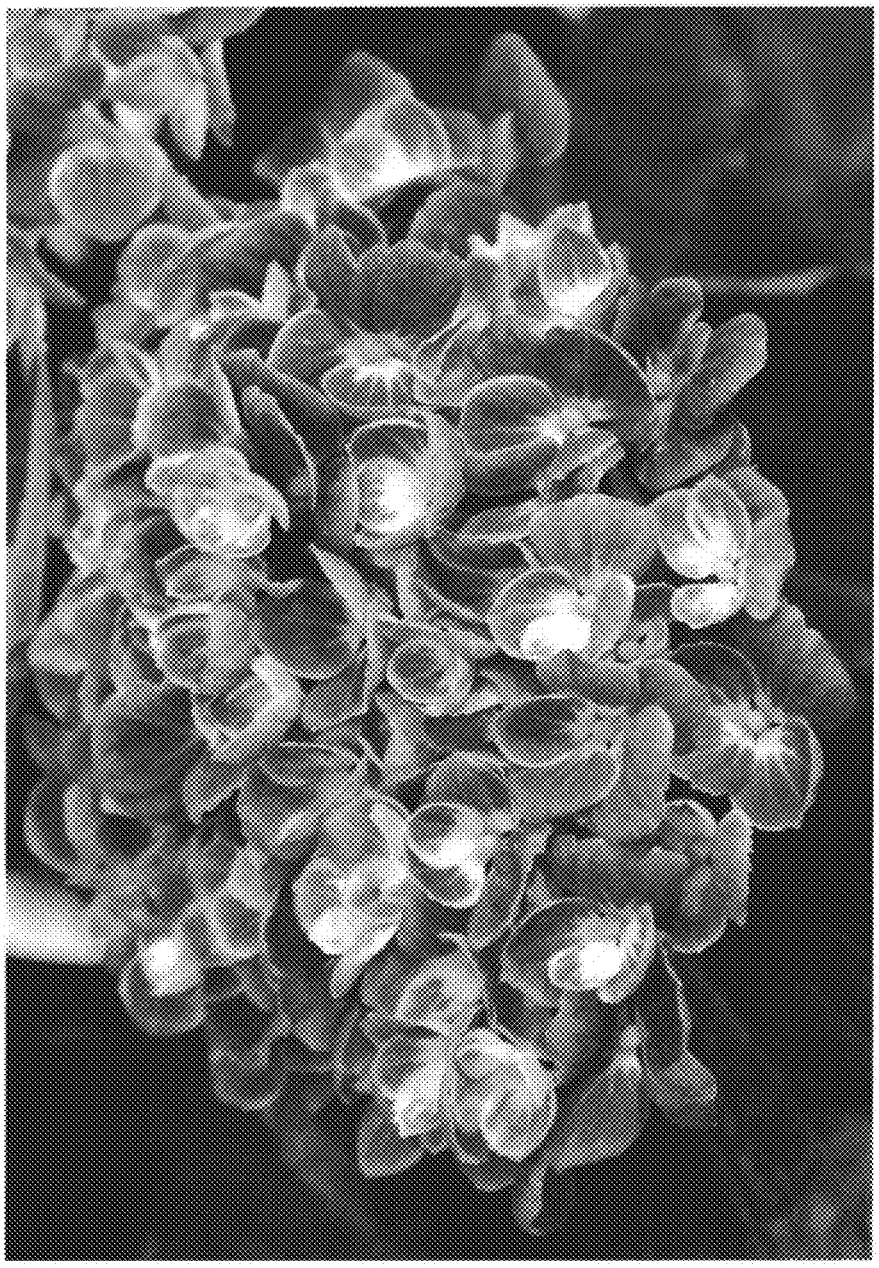

The photograph on the second sheet (FIG. 2 of 2) is a close-up view of a typical inflorescence of 'Hokomagrevo'.

DETAILED BOTANICAL DESCRIPTION

Plants used in the aforementioned photographs and in the following description were grown during the summer in 17-cm containers in a glass-covered greenhouse in Boskoop, The Netherlands and under cultural practices typical of commercial *Hydrangea* production. During the production of the plants, day temperatures ranged from 20° C. to 35° C. and night temperatures ranged from 10° C. to 22° C. Plants of the new *Hydrangea* were two years old when the photographs and description were taken. Plants of the new *Hydrangea* are not typically treated with aluminum sulfate to "blue" the inflorescences. In the following description, color references are made to The Royal Horticultural Society Colour Chart, 2015 Edition, except where general terms of ordinary dictionary significance are used.

Botanical description: *Hydrangea macrophylla* 'Hokomagrevo'.

Parentage: Naturally-occurring whole plant mutation of *Hydrangea macrophylla* 'Hokomarore', disclosed in U.S. Plant Pat. No. 22,260.

Propagation:

*Type cutting*.—By vegetative terminal cuttings.

*Time to initiate roots, summer*.—About four weeks at temperatures about 15° C. to 25° C.

*Time to initiate roots, winter*.—About six weeks at temperatures about 15° C. to 21° C.

*Time to produce a rooted young plant, summer*.—About 100 days at temperatures about 15° C. to 25° C.

*Time to produce a rooted young plant, winter*.—About 140 days at temperatures about 15° C. to 21° C.

*Root description*.—Medium in thickness, fibrous; typically creamy white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Compact, upright and somewhat outwardly spreading plant habit; overall plant shape, obovate to broadly obovate; strong and sturdy lateral branches; moderately vigorous to vigorous growth habit and moderate growth rate.

*Plant height*.—About 42.8 cm.

*Plant diameter or area of spread*.—About 55 cm.

Lateral branch description:

*Branching habit*.—Freely branching habit about 17 lateral branches develop per plant; pinching will enhance branching.

*Length*.—About 22.5 cm.

*Diameter*.—About 5 mm.

*Internode length*.—About 5.9 cm.

*Texture*.—Smooth, glabrous; fully developed, woody.

*Aspect*.—Varying from upright to about 55° from vertical.

*Strength*.—Strong, sturdy.

*Color*.—When developing: Close to 144A. Developed: Close to 144A; at the internodes, occasionally moderately tinged with close to N186B; when woody, close to 199B to 199C.

*Lenticels*.—Density: Dense. Length: About 2.5 mm. Diameter: About 1 mm. Color: Close to N186B.

Leaf description:

*Arrangement*.—Opposite, simple.

*Length*.—About 11 cm.

*Width*.—About 8.1 cm.

*Shape*.—Broadly ovate to broadly elliptic.

*Apex*.—Short apiculate.

*Base*.—Short attenuate to obtuse.

*Margin*.—Coarsely serrate.

*Texture, upper surface*.—Smooth to slightly rugose, glabrous.

*Texture, lower surface*.—Smooth to moderately rugose, glabrous.

*Venation pattern*.—Pinnate.

*Color*.—Developing leaves, upper surface: Close to between 137B and 143A. Developing leaves, lower surface: Close to 144A. Fully expanded leaves, upper surface: Close to between NN137A and 139A;

venation, close to 144A. Fully expanded leaves, lower surface: Close to 147B; venation, close to 146D.

*Petioles*.—Length: About 2 cm. Diameter: About 3.5 mm. Texture and luster, upper and lower surfaces: Smooth, glabrous; slightly glossy. Color, upper surface: Close to 144B; towards the margins, close to 144A. Color, lower surface: Close to 144A.

Flower description:

*Flower type and habit*.—Showy sterile flowers and small inconspicuous fertile flowers arranged on mophead-type terminal panicles; panicles flattened globular in shape; fertile flowers face mostly upright and sterile flowers face upright to outwardly depending on their position in the inflorescence; fertile flowers have not been observed to develop beyond the bud stage.

*Fragrance*.—None detected.

*Natural flowering season*.—Plants flower from late spring to late summer in The Netherlands.

*Flower longevity*.—Fertile flowers last about ten days on the plant, fertile flowers not persistent; sterile flowers last about six weeks on the plant, sterile flowers persistent.

*Quantity of flowers*.—Freely flowering habit; about 100 fertile flowers develop per panicle and about 230 sterile flowers develop per panicle.

*Panicle height*.—About 10.9 cm.

*Panicle diameter*.—About 15.1 cm.

*Fertile flower buds*.—Length: About 4 mm. Diameter: About 2.5 mm. Shape: Obovate to ovate. Color: Close to N187D; towards the base, close to 145D; immature sepals, close to 145B.

*Sterile flower buds*.—Length: About 9 mm. Diameter: About 1.1 cm. Shape: Narrowly cup-shaped. Color: Close to between 144B and 145A fading towards the base to close to 150D.

*Fertile flower diameter*.—About 4 mm.

*Fertile flower depth* (*height*).—About 2.5 mm.

*Sterile flower diameter*.—About 2.2 cm.

*Sterile flower depth* (*height*).—About 9 mm.

*Petals, fertile flowers*.—Quantity and arrangement: Four in a single whorl; petals have not been observed to develop beyond the flower bud stage. Length: About 4 mm. Width: About 2.5 mm. Texture and luster, upper and lower surfaces: Smooth, glabrous; matte. Color, upper and lower surfaces: Close to 195B to 195C.

*Petals, sterile flowers*.—Quantity and arrangement: Four in a single whorl; petals have not been observed to develop beyond the flower bud stage. Texture and luster, upper and lower surfaces: Smooth, glabrous; matte. Color, upper and lower surfaces: Close to 76D.

*Sepals, fertile flowers*.—Quantity and arrangement: About five in a single whorl. Length: About 2 mm. Width: About 1.5 mm. Shape: Obovate. Apex: Broadly acute. Base: Broadly cuneate. Margin: Entire. Texture and luster, upper surface: Smooth, glabrous; matte. Texture and luster, lower surface: Smooth, glabrous; slightly glossy. Color: When opening and fully opened, upper surface: Close to 150D; color does not change with development. When opening and fully opened, lower surface: Close to 144C; towards the base and the margins, close to 150D; color does not change with development.

*Sepals, sterile flowers*.—Quantity and arrangement: Four, or occasionally three, in a single whorl. Length: About 1.4 cm. Width: About 1.4 cm. Shape: Reniform, convex. Apex: Broadly ovate to reniform. Base: Broadly cuneate to truncate. Margin: Shallowly serrate to entire. Texture and luster, upper and lower surfaces: Smooth, glabrous; matte. Color: When opening, upper surface: Close to 144A; towards the base, close to 75C; towards the margins, close to NN155B. When opening, lower surface: Close to 146D; towards the base, close to NN155B tinged with close to 75B to 75C; towards the margins, close to NN155B. Fully opened, upper surface: Close to 144A, 144B and N144C; towards the base, close to NN155B slightly tinged with close to 75C; color becoming closer to 143A with development. Fully opened, lower surface: Close to 146C and 147C; towards the base, close to NN155B tinged with close to 75C; towards the margins, close to NN155B; color becoming closer to 146D with development.

*Pedicels, fertile flowers*.—Length: About 2.5 mm. Diameter: About 1 mm. Strength: Moderately strong. Aspect: About 27.5° from vertical. Texture and luster: Slightly pubescent; matte. Color: Lighter than between 174D and 177D.

*Pedicels, sterile flowers*.—Length: About 2.1 cm. Diameter: About 1 mm. Strength: Moderately strong. Aspect: About 30° from vertical. Texture and luster: Moderately pubescent; matte. Color: Close to 60C; fading proximally to close to 177B to 177C.

*Reproductive organs, fertile flowers*.—Stamens: To date, stamen development has not been observed on plants of the new *Hydrangea*. Pistils: To date, pistil development has not been observed on plants of the new *Hydrangea*.

*Reproductive organs, sterile flowers*.—Stamens: To date, stamen development has not been observed on plants of the new *Hydrangea*. Pistils: To date, pistil development has not been observed on plants of the new *Hydrangea*.

*Seeds*.—To date, seed development has not been observed on plants of the new *Hydrangea*.

Pathogen & pest resistance: To date, under commercial production conditions, plants of the new *Hydrangea* have not been observed to be resistant to pathogens and pests common to *Hydrangea* plants.

Temperature tolerance: Plants of the new *Hydrangea* have been observed to tolerate temperatures ranging from −20° C. to 35° C. and are suitable for USDA Hardiness Zones 5 to 9.

It is claimed:

1. A new and distinct *Hydrangea* plant named 'Hokomagrevo' as illustrated and described.

* * * * *